(12) United States Patent
Antons et al.

(10) Patent No.: US 8,754,262 B2
(45) Date of Patent: Jun. 17, 2014

(54) PROCESS FOR PREPARING 2,2-DIFLUOROETHYLAMINE BY HYDROGENATING 1,1-DIFLUORO-2-NITROETHANE

(75) Inventors: Stefan Antons, Leverkusen (DE); Norbert Lui, Odenthal (DE); Arne Gerlach, Düsseldorf (DE)

(73) Assignee: Bayer CropScience AG, Monheim (DE)

( * ) Notice: Subject to any disclaimer, the term of this patent is extended or adjusted under 35 U.S.C. 154(b) by 475 days.

(21) Appl. No.: 12/899,028

(22) Filed: Oct. 6, 2010

(65) Prior Publication Data

US 2011/0082318 A1 Apr. 7, 2011

Related U.S. Application Data

(60) Provisional application No. 61/249,815, filed on Oct. 8, 2009.

(30) Foreign Application Priority Data

Oct. 6, 2009 (EP) .................................... 09172271

(51) Int. Cl.
C07C 209/00 (2006.01)

(52) U.S. Cl.
USPC ........................................................ 564/494

(58) Field of Classification Search
None
See application file for complete search history.

(56) References Cited

U.S. PATENT DOCUMENTS

| 4,533,776 A | 8/1985 | Baasner et al. | |
|---|---|---|---|
| 2006/0149097 A1* | 7/2006 | Soled et al. | 562/487 |

FOREIGN PATENT DOCUMENTS

EP 0 116 886 A1 8/1984

OTHER PUBLICATIONS

Knunyants, I. et al. "Aliphatic fluoro nitro compounds. Communication 4. Reduction of polyfluoronitroalkanes," Izvestiya Akademii Nauk USSR (1966) English translation, pp. 226-228.*
Cook, D. J., et al., "The Preparation and Reactions of Some Fluorine-containing Nitro Compounds," *J. Am. Chem. Soc.* 76:83-87, American Chemical Soceity, United States (1954).
Dickey, J. B., et al., "Fluorinated Aminoanthraquinone Dyes," *Industrial and Engineering Chemistry Product Research and Development* 48:209-213, American Chemical Society, United States (1956).
Donetti, A., et al., "$N$ -(Fluoroethyl)(imidazolylphenyl) formamidines. The Issue of the Active Species of Mifentidine," *J. Med. Chem.* 32:957-961, American Chemical Society, United States (1989).
Feiring, A. E., "Perfluoralkylation of the 2-Nitropropyl Anion. Evidence for an $S_{RN}$ 1 Process," *J. Org. Chem.* 48:347-354, American Chemical Society, United States (1983).
Kluger, R. and Chin, J., "Carboxylic Acid Participation in Amide Hydrolysis Evidence That Separation of a Nonbonded Complex Can Be Rate Determining," *J. Am. Chem. Soc.* 104:2891-2897, American Chemical Society, United States (1982).
Pattison, F. L. M., et al., "Toxic Fluoride Compounds. VI.[1] ω-Flouralkylamines,"*J. Am. Chem. Soc.* 78:3487-3489, American Chemical Society, United States (1954).
Ram, S. and Ehrenkaufer, R. E., "A General Procedure for Mild and Rapid Reduction of Aliphatic and Aromatic Nitro Compounds Using Ammonium Formate as a Catalytic Hydrogen Transfer Agent," *Tetrahedron Lett.* 25:3415-3418, Pergamon Press Ltd., England (1984).
Shao, Y.-M., et al., "Design, synthesis, and evaluation of trifluoromethyl ketones as inhibitors of SARS-CoV 3CL protease," *Bioorg. Med. Chem.* 16:4652-4660, Elsevier, England (2008).
Swarts, F., "Über einige flourhaltige Alkylamine," *Chemisches Zentrablatt* 75(II):944-945, Germany (1904).
International Search Report for International Application Patent No. PCT/EP2010/064700, European Patent Office, Netherlands, mailed on May 6, 2011.

\* cited by examiner

*Primary Examiner* — Sudhakar Katakam
(74) *Attorney, Agent, or Firm* — Sterne, Kessler, Goldstein & Fox P.L.L.C.

(57) ABSTRACT

Process for preparing 2,2-difluoroethylamine, characterized in that 1,1-difluoro-2-nitroethane is subjected to a catalytic hydrogenation.

6 Claims, No Drawings

PROCESS FOR PREPARING 2,2-DIFLUOROETHYLAMINE BY HYDROGENATING 1,1-DIFLUORO-2-NITROETHANE

The present invention relates to a process for preparing 2,2-difluoroethylamine and/or acid addition salts thereof, comprising the catalytic hydrogenation of 1,1-difluoro-2-nitroethane.

2,2-Difluoroethylamine is an important intermediate compound in active ingredient preparation. Various preparation methods for 2,2-difluoroethylamine are known.

Donetti et al. (J. Med. Chem. 1989, 32, 957-961) describe the synthesis of 2,2-difluoroethylamine hydrochloride proceeding from 2,2-difluoroacetamide. The desired amine is prepared here with a diborane solution in tetrahydrofuran (THF). The yield is 48%.

Kluger et al. (JACS 1982, 104, 10, 2891-2897) describe the synthesis of 2,2-difluoroethylamine proceeding from the amide with sodium boronate and boron trifluoride etherate. The yield is 60%.

Kollonitsch (U.S. Pat. No. 4,030,994) also describes a synthesis of 2,2-difluoroethylamine, namely the reaction of ethylamine with fluoroxytrifluoromethane in hydrogen fluoride under UV irradiation.

The preparation of 2,2-difluoroethylamine is also described in Dickey et al. (Ind. Eng. Chem. 1956, 209-213). 2,2-Difluoro-1-chloroethane is reacted therein with 28% ammonium hydroxide, i.e. 28% aqueous ammonia solution, in an autoclave. The amine was thus obtained in a yield of 65%.

None of these processes can be performed on the economically viable industrial scale. The low yield and the use of expensive and hazardous chemicals, for example sodium boronate/$BF_3$ or diborane, prevent suitability of the process according to Donetti et al. and Kluger et al. for the industrial scale preparation of 2,2-difluoroethylamine. The process according to Kollonitsch et al. uses hazardous chemicals, and impure 2,2-difluoroethylamine is obtained. The process according to Dickey et. al. is likewise unsuitable for industrial use or uneconomic since it requires a very long reaction time for a relatively low yield. Moreover, the reaction mixture is highly corrosive and so economic viability is questionable for that reason, too.

Proceeding from the known processes for preparing 2,2-difluoroethylamine, it is an object of the present invention to find an alternative process by which 2,2-difluoroethylamine can be prepared simply and inexpensively. Inexpensive processes are understood to mean processes which are performable without any great financial investment, because the starting materials, for example, are non-hazardous and/or the desired 2,2-difluoroethylamine is obtained in sufficiently high yield and purity. Equally it is advantageous to obtain the corresponding 2,2-difluoroethylamine acid addition salts, since they can be converted directly to 2,2-difluoroethylamine.

1,1-Difluoro-2-nitroethane is readily available as a starting material, since it can be prepared in high yield and in good purity with the process described in DE-A1-3305201. Accordingly it would be desirable to find a process in which 1,1-difluoro-2-nitroethane is reduced to the desired amine.

Knunyants et al. ("Aliphatic Fluoro Nitro Compounds Communication 3", Russian Chemical Bulletin (1964), Seiten 1538-1541) describe the catalytic hydrogenation of alkoxyfluoronitropropanes over Raney-nickel, a solid catalyst which consists of fine grains of an aluminum-nickel alloy, in the presence of gaseous hydrogen to give 1-(alkoxymethyl)-2,2,2-trifluoroethylamine. In particular, the hydrogenation of 1-(ethoxymethyl)-2,2,2-trifluoroethylamine with gaseous hydrogen over Raney-nickel in an autoclave at a hydrogen pressure of 60 atm (approximately 60 bar) was described. After the working up 1-(ethoxymethyl)-2,2,2-trifluoroethylamine has been isolated as hydrochlorid in a yield of 77%.

Knunyants et al. (in Izvestiya Akademii Nauk SSSR (1966), (2), pages 250-253 in Russian language and in Russian Chemical Bulletin (1966), "Aliphatic Fluoro Nitro Compounds Communication 4", pages 226-228 in English) describe methods for hydrogenating fluorinated nitrohydrocarbons, especially 1,1,1-trifluoro-2-nitroethane, using metallic palladium or iron in hydrochloric acid, with the aim of obtaining the corresponding amine. While the use of metallic palladium in the reduction of 1,1,1-trifluoro-2-nitroethane leads merely to N-(2,2,2-trifluoroethyl)hydroxylamine, the desired 2,2,2-trifluoroethylamine hydrochloride can be obtained with 77% yield when iron in hydrochloric acid is used. This involves heating 1,1,1-trifluoro-2-nitroethane together with hydrochloric acid and iron filings at 90 to 95° C., then alkalizing with sodium hydroxide and distilling out the trifluoroethylamine with steam. The product is isolated as the hydrochloride.

Knunyants et al. (1966), however, describe the catalytic hydrogenation of 1,1-difluoro-2-nitroethane. It has been found that the reduction and hydrogenation methods described in Knunyants et al. cannot be applied directly to the reduction of 1,1-difluoro-2-nitroethane. Thus, the reduction hydrogenation of 1,1-difluoro-2-nitroethane with iron in hydrochloric acid under the conditions described in Knunyants did not lead to 2,2-difluoroethylamine.

A process has now been found for catalytic hydrogenation of 1,1-difluoro-2-nitroethane, by which 2,2-difluoroethylamine or a corresponding acid addition salt can be prepared in good yields and high purity, such that generally no complex purifications are required subsequently, and which at the same time is simple and inexpensive.

The invention thus provides a process for preparing 2,2-difluoroethylamine and/or acid addition salts thereof comprising the catalytic hydrogenation of 1,1-difluoro-2-nitroethane.

The process according to the invention is illustrated by way of example in the following scheme:

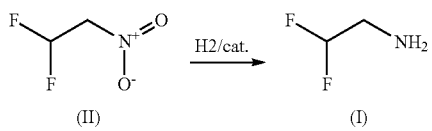

The inventive catalytic hydrogenation takes place in the presence of a catalyst, with gaseous hydrogen being introduced into the reaction vessel or being generated in situ in the reaction vessel.

Suitable catalysts to be used for the catalytic hydrogenation according to the invention comprise one or more metals of groups 8-10 of the Periodic Table, especially one or more metals selected from iron, ruthenium, osmium, cobalt, rhodium, iridium, nickel, palladium and platinum. Besides their catalytic activity, suitable catalysts are under the selected reaction conditions inert. The metals may be present in any chemical form, for example in elemental, colloidal, salt or oxide form, together with complexing agents as chelates, or as alloys, in which case the alloys may also include other metals, for example aluminium, as well as the metals listed above. The metals may be present in supported form, i.e. applied to any support, preferably an inorganic support. Examples of suitable supports are carbon (charcoal or activated carbon), aluminium oxide, silicon dioxide, zirconium dioxide or titanium dioxide. Catalysts preferred in accordance with the invention contain one or more metals of groups 8-10 of the Periodic Table on an inorganic support. Particular preference is given in accordance with the invention to catalysts which include platinum and/or palladium, and are optionally applied to an inorganic support. Such catalysts are, for example, $PtO_2$, $Pd(OH)_2$ on activated carbon (Pearlman-type catalyst), and Lindlar catalysts. The use of Raney-nicke is not favourable, since it is not stable under acidic conditions. The nickel is removed from the alloy and, together with the anion of the acid, forms the corresponding nickel salt. Hence, Raney-nicke excluded from being a suitable catalyst according to the invention.

In the process according to the invention, the catalyst is used, based on the 1,1-difluoro-2-nitroethane used, in a concentration of about 0.01 to about 30% by weight. The catalyst is preferably used in a concentration of about 0.1 to about 25% by weight.

In the process according to the invention, it is usual to initially charge 1,1-difluoro-2-nitroethane and the catalyst in a first step (i), and to introduce or generate hydrogen in a second step (ii). The reversal of steps (i) and (ii) is possible. It is also possible to hydrogenate continuously or batchwise.

The catalytic hydrogenation can be performed under elevated pressure (i.e. up to about 200 bar) in an autoclave, or at standard pressure in a hydrogen gas atmosphere. Especially at high reaction temperatures, it may be helpful to work at elevated pressure. The (additional) pressure increase can be brought about by supply of an inert gas, such as nitrogen or argon. The inventive hydrogenation is effected preferably at a pressure in the range from about 1 to about 30 bar, more preferably at a pressure in the range from about 5 to about 25 bar.

In one embodiment of the invention, a sufficient amount of inorganic or organic acid or mixtures thereof is added after hydrogenation and optionally after removal of the catalyst. Suitable acids are, for example hydrochloric acid, sulphuric acid, formic acid or acetic acid. This makes it possible to obtain the corresponding acid addition salt of 2,2-difluoroethylamine, which is then isolated as described here and/or converted to the free 2,2-difluoroethylamine.

In a further embodiment of the invention, the catalytic hydrogenation takes place in the presence of a sufficient amount of inorganic or organic acids or mixtures thereof. Suitable acids are, for example, hydrochloric acid, sulphuric acid, formic acid or acetic acid. In this embodiment, the catalyst must not be acid-sensitive. Preferred hydrogenation catalysts are therefore especially catalysts comprising platinum and/or palladium. The acid can be added in concentrated form or with water. Preference is given to adding the acid to the reaction mixture before hydrogenation, such that a solvent-acid mixture is present in the ideal case. The presence of the acid leads to the effect that the product formed by hydrogenation is converted immediately to the corresponding acid addition salt of 2,2-difluoroethylamine, the result being that a lower level of by-products forms, which increases the yield. Reaction times of fewer than 20 hours also already lead to good yields. The acid addition salt formed is then isolated as described here and/or converted to the free 2,2-difluoroethylamine.

According to the invention, a sufficient amount of inorganic or organic acids or mixtures thereof is understood to mean the amount with which the 2,2-difluoroethylamine product is present completely in protonated form. In the case of monobasic acids (e.g. HCl) at least one equivalent of acid is required, and in the case of dibasic acids (such as $H_2SO_4$) at least 0.5 equivalent, based on the 1,1-difluoro-2-nitroethane used.

It is generally advantageous to perform the process according to the invention in the presence of solvents (diluents). However, the catalytic hydrogenation can also be performed without a solvent. Solvents are advantageously used in such an amount that the reaction mixture remains efficiently stirrable over the entire process. Advantageously, based on the 1,1-difluoro-2-nitroethane used, 1 to 50 times the amount of solvent, preferably 2 to 40 times the amount of solvent and more preferably 2 to 30 times the amount of solvent is used.

Useful solvents for performance of the process according to the invention include all organic solvents which are inert under the reaction conditions, the type of solvent used depending on the type of reaction procedure, more particularly on the type of catalyst used and/or the hydrogen source (introduction of gaseous hydrogen or generation in situ). Solvents are also understood in accordance with the invention to mean mixtures of pure solvents.

Solvents suitable in accordance with the invention are especially halohydrocarbons, e.g. chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols such as methanol, ethanol, isopropanol, butanol; ethers, such as ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, dioxane, dichlorodiethyl ether, and polyethers of ethylene oxide and/or propylene oxide; aliphatic, cycloaliphatic or aromatic hydrocarbons such as pentane, hexane, heptane, octane, nonane, and technical-grade hydrocarbons which may be substituted by fluorine and chlorine atoms, such as methylene chloride, dichloromethane, trichloromethane, carbon tetrachloride, fluorobenzene, chlorobenzene or dichlorobenzene; for example white spirits having components with boiling points in the range, for example, from 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, xylene; esters such as methyl acetate, ethyl acetate, butyl acetate, isobutyl acetate, and also dimethyl carbonate, dibutyl carbonate or ethylene carbonate. Another inventive solvent is water.

In the process according to the invention, the solvents used are preferably chlorohydrocarbons or alcohols.

The process according to the invention can be performed within a wide temperature range (for example in the range from about −20° C. to about 100° C.). Preference is given to performing the catalytic hydrogenation within a temperature range from about 0° C. to about 40° C.

The reaction time of the inventive hydrogenation is generally between 30 minutes and 24 hours. Longer reaction times are possible and do not have any adverse effects, but are not advantageous from an economic standpoint.

When the 2,2-difluoroethylamine is present in free form after the catalytic hydrogenation, it is purified by distillation if necessary. When 2,2-difluoroethylamine is present as an acid addition salt after the catalytic hydrogenation, it is purified, if necessary, preferably by crystallization.

Water-soluble acid addition salts of 2,2-difluoroethylamine are generally purified by extraction from an aqueous solution. The free 2,2-difluoroethylamine is released by reacting the corresponding acid addition salt with organic or inorganic bases (e.g. $NaHCO_3$, $Na_2CO_3$ or NaOH). Subsequently, the difluoroethylamine is distilled directly out of the aqueous solution or extracted into an organic solvent.

The present invention is illustrated in detail with reference to the examples which follow, though the examples should not be interpreted in such a manner as to restrict the invention.

PREPARATION EXAMPLES

Example 1

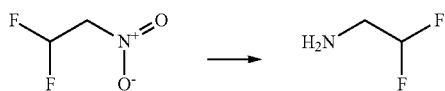

5 mmol of 1,1-difluoro-2-nitroethane are initially charged in methanol and admixed with 20% by weight of $PtO_2$ under nitrogen. The reaction mixture is stirred at room temperature (about 20° C.) and a pressure of 20 bar of hydrogen for 16 hours. After the hydrogenation mixture has been cooled to 0° C., the pressure is released, i.e. decompressed, and the catalyst is filtered off. Then 7.5 mmol of HCl dissolved in methanol are added. After the solvent, methanol here, has been removed under reduced pressure, 560 mg of 80% hydrochloride of 2,2-difluoroethylamine are obtained in solid form. This corresponds to a yield of 80% of theory.

NMR (MeOD): 6.19 to 6.0 ppm (m, 1H) 3.2-3.13 (m, 2H); $M^+$: 81

Example 2

5 mmol of 1,1-difluoro-2-nitroethane are initially charged in methanol together with 1.5 equivalents of hydrochloric acid and admixed with 20% by weight of $PtO_2$ under nitrogen. The reaction mixture is stirred at room temperature (about 20° C.) and a pressure of 20 bar of hydrogen for 7 hours. After the hydrogenation mixture has been cooled to 0° C., the pressure is released, i.e. decompressed, and the catalyst is filtered off. Then 7.5 mmol of HCl dissolved in methanol are added. After the solvent, methanol here, has been removed under reduced pressure, 560 mg of 95% hydrochloride of 2,2-difluoroethylamine are obtained in solid form. This corresponds to a yield of 95% of theory.

NMR (MeOD): 6.19 to 6.0 ppm (m, 1H) 3.2-3.13 (m, 2H); M+: 81

Example 3

A 25 ml hydrogenation autoclave (material: Hastelloy, mechanical propeller stirrer) is initially charged with 1.0 g (0.007 mol, 1.0 equivalent) of difluoronitroethane (approx. 80% solution in dichloromethane) in 9 ml of ethanol together with 0.880 g (0.009 mol, 1.3 equivalent) of concentrated sulphuric acid and 0.100 g of 20% $Pd(OH)_2$ on activated carbon (Pearlman-type catalyst). After flushing with hydrogen, hydrogenation is effected at room temperature and 20 bar of hydrogen for approx. 3 hours (stirrer speed approx. 600 rpm). After filtration and washing the catalyst, 16.6 g of a pale yellow reaction mixture are obtained. After analysis by means of quantitative NMR, a yield of 90% is obtained.

Example 4

A 25 ml hydrogenation autoclave (material: Hastelloy, mechanical propeller stirrer) is initially charged with 2.0 g (0.010 mol, 1.0 equivalent) of difluoronitroethane (approx. 60% solution in dichloromethane) in 9 ml of water together with 1.270 g (0.013 mol, 1.3 equivalent) of concentrated sulphuric acid and 0.100 g of 20% $Pd(OH)_2$ on activated carbon (Pearlman-type catalyst). After flushing with hydrogen, hydrogenation is effected at room temperature and 20 bar of hydrogen for approx. 3 hours (stirrer speed approx. 600 rpm). After filtration and washing the catalyst, 17.8 g of a pale yellow reaction mixture are obtained. After analysis by means of quantitative NMR, a yield of 88% is obtained.

Comparative Example 1

5 mmol of 1,1-difluoro-2-nitroethane are initially charged in a mixture of methanol and concentrated acetic acid (=glacial acetic acid) in a ratio of 4:1, and admixed with 20% by weight of Raney nickel under nitrogen. The reaction mixture is stirred at room temperature (about 20° C.) and a pressure of 20 bar of hydrogen for 7 hours. After the hydrogenation mixture has been cooled to 0° C., the pressure is released, i.e. decompressed, and the catalyst is filtered off. Then the solvent, methanol here, is removed under reduced pressure to obtain 560 mg of 95% 2,2-difluoroethylamine in solid form. This corresponds to a yield of 80% of theory. 2,2-Difluoroethylamine is present here as a mixture of monoacetyl-2,2-difluoroethylamine and the acetate salt thereof. The Raney-nickel catalyst can not be fully recovered as the nickel reacts with the acetic acid and leads to nickel acetate.

$^{13}$C-NMR (MeOD) monoacetyl-2,2-difluoroethylamine: —$CHF_2$ (115.3 ppm); —$CH_2$ (42.7 ppm), $CO_2$— (173.9 ppm); —$CH_3$ (22.3 ppm)

$^{13}$C-NMR (MeOD) 2,2-difluoroethylamine as the acetate salt: —$CHF_2$ (115.4 ppm); —$CH_2$ (43 ppm), $CO_2$— (176.5 ppm); —$CH_3$ (21.7 ppm)

Comparative Example 2

11.1 g (0.1 mol of difluoronitroethane, 0.1 g of iron chloride, 23 g of iron filings are heated under reflux in a mixture of 50 ml of concentrated hydrochloric acid and 80 ml of water for 2 h. The reaction mixture is subsequently admixed with 32 g of NaOH in 100 ml of water. After steam distillation, the distillate is acidified with hydrochloric acid and concentrated under reduced pressure. It was not possible to isolate any difluoroethylamine hydrochloride.

The invention claimed is:

1. A process for preparing 2,2-difluoroethylamine, which comprises subjecting 1,1-difluoro-2-nitroethane to a catalytic hydrogenation, wherein the catalyst used in the catalytic hydrogenation comprises a metal selected from the group consisting of palladium and platinum under the proviso that Raney nickel is excluded.

2. The process according to claim 1, wherein the catalytic hydrogenation takes place in the presence of inorganic or organic acid.

3. The process according to claim 1, wherein the catalyst is $PtO_2$, $Pd(OH)_2$ on activated carbon, or a Lindlar catalyst.

4. The process according to claim 1, wherein the catalytic hydrogenation involves introducing gaseous hydrogen into the reaction vessel or generating hydrogen in situ.

5. The process according to claim 2, wherein the catalyst is $PtO_2$, $Pd(OH)_2$ on activated carbon, or a Lindlar catalyst.

6. The process according to claim 2, wherein the catalytic hydrogenation involves introducing gaseous hydrogen into the reaction vessel or generating hydrogen in situ.

* * * * *